United States Patent [19]

Pathak et al.

[11] 4,309,408

[45] Jan. 5, 1982

[54] EFFERVESCENT POWDERS

[75] Inventors: Ram D. Pathak, Worcester Park; Elizabeth J. Treherne, Surry, both of England

[73] Assignee: Beecham Group Limited, England

[21] Appl. No.: 92,924

[22] Filed: Nov. 9, 1979

[30] Foreign Application Priority Data

Nov. 16, 1978 [GB] United Kingdom ............... 44839/78

[51] Int. Cl.³ ...................... A61K 31/165; A61L 9/04
[52] U.S. Cl. ....................................... 424/44; 424/324
[58] Field of Search .................................. 424/324, 44

[56] References Cited

U.S. PATENT DOCUMENTS

3,136,669  6/1964  Bandelin ............................ 167/57

FOREIGN PATENT DOCUMENTS

769156  6/1970  Belgium .
2013552  4/1970  France .
2085730  12/1971  France .
2187312  1/1974  France .
1442159  7/1976  United Kingdom .

OTHER PUBLICATIONS

Chem. Abst., vol. 78–58100j, (1973).
Chem. Abst., vol. 82–106539r, (1975).
*DRUGS*, 12, 1976, p. 100.
Chem. Abst., 84–1598096, (1976).
Chem. Abst., 83–37899q, (1975).

*Primary Examiner*—Stanley J. Friedman
*Attorney, Agent, or Firm*—Jacobs & Jacobs

[57] ABSTRACT

Effervescent analgesic powders which comprise paracetamol D.C., and metoclopramide or an acid addition salt thereof, the weight ratio of paracetamol D.C. to metoclopramide or the acid addition salt thereof lying in the range 50:1 to 250:1, and a process for their preparation.

5 Claims, No Drawings

EFFERVESCENT POWDERS

This invention relates to effervescent powders containing a certain paracetamol and metoclopramide or an acid addition salt thereof, and to a process for the preparation of these powders.

It is known that metoclopramide, parenterally administered, potentiates the effect of an orally administered analgesic.

Surprisingly we have now found that the simultaneous oral administration of a specific formulation containing a certain paracetamol and metoclopramide or a salt thereof is benificial in the treatment of migraine headache.

Accordingly, the present invention provides an effervescent analgesic powder, which powder comprises paracetamol D.C., and metoclopramide or an acid addition salt thereof, the weight ratio of paracetamol D.C. to metoclopramide or the acid addition salt thereof lying in the range 50:1 to 250:1.

Paracetamol D.C. is specifically indicated and well known in the formulation art and commercially available for use in direct compression tablets. It is paracetamol coated with hydrolysed gelatin to aid compression formulation. We believe it to be a particularly surprising feature of this invention that a material specifically made and known for tabletting use maybe used to great advantage in a powder formulation.

Used in the manner of this invention the paracetamol D.C. has a number of advantages, such as good wettability.

The acid addition salt of metoclopramide is suitably any pharmaceutically acceptable salt such as the hydrochloride.

The powders are usually rendered effervescent by means of an effervescent couple, such as the combination of a water-soluble inorganic bicarbonate and a solid aliphatic carboxylic acid or preferably an acid salt thereof.

The water-soluble inorganic bicarbonate is preferably an alkali metal bicarbonate, and more suitably sodium or potassium bicarbonate.

Suitable solid aliphatic carboxylic acids include polybasic acids such as citric and adipic acids, but any solid aliphatic carboxylic acid which does not give rise to undesirable effects in combination with the other materials of the powder may be employed. Suitable acids will be known to the skilled man or will be readily and routinely ascertainable as such.

Suitable acid salts thereof include incompletely salified alkali metal salts of the above polybasic acids, preferably the sodium or potassium salts.

The presence of water tends to initiate the reaction of the bicarbonate and acid or acid salt present, with deleterious results, since this reaction is 'autocatalytic' by virtue of its producing water as a by-product.

Accordingly, anhydrous acids or acid salts thereof are preferred, such as anhydrous citric acid.

The metoclopramide or its acid addition salt is suitably present as 0.03 to 0.5 percent by weight of the powder, preferably as 0.05 to 0.4 percent by weight.

The weight ratio of paracetamol D.C. to metoclopramide suitably lies in the range of 60:1 to 140:1, preferably in the range 80:1 to 120:1.

The powders will conveniently be presented in unit form, for example in a sachet containing a unit dose of each medicament. However, multiples or sub-multiples of such unit doses may be incorporated as desired in the powder units.

It will be appreciated that it will often be convenient to incorporate half a unit dose of each medicament in each powder unit.

Suitable unit doses of the paracetamol D.C. lie in the range of 0.6 to 1.4 g., more generally 0.8 to 1.2 g.

Suitable unit doses of metoclopramide or an acid addition salt thereof lie in the range 5 to 15 mg, more generally 8 to 12 mg.

The powder may contain other components conventionally used in the art of effervescent powder formulation such as flavourings, sweeteners, colourants and desiccants such as anhydrous sodium carbonate.

The powders will be made up for administration by dissolution in water. Suitably about 50 ml of water will be used per unit dose of powder.

The present invention also provides a process for the preparation of the present powders, which process comprises bringing into association the paracetamol D.C., metoclopramide or acid addition salt thereof and effervescent materials.

Other conventional powder ingredients maybe included in the mixture if so desired.

Usually for even distribution of a minor component by weight in a pharmaceutical formulation it is necessary or highly desirable to wet granulate the minor component with a major components and then, after drying the resultant granulate, to mix it with the other formulation components.

Thus the metoclopramide or salt thereof in the present formulations may be wet granulated with the acid part of the effervescent couple, for example by adding a solution of the metoclopramide or salt thereof to the powdered acid or acid salt and subjecting the mixture to a wet granulation process.

However, we have surprisingly found that good distribution is obtained without granulation, that is by simple mixing of the components. Such mixing is a preferred process for the preparation of the present powders.

The powders also give relief of gastro-intestinal symptoms associated with migrane.

The following Examples illustrate the preparation of the powders of the present invention.

TABLE

| Ingredients | weight, mg Formulation | | | |
| --- | --- | --- | --- | --- |
| | A | B | C | D |
| Paracetamol D.C. (96% pure) | 520 | 520 | 520 | 520 |
| Metoclopramide hydrochloride monohydrate B.P. | 5.25 | 5.25 | 5.3 | 5.3 |
| Sodium bicarbonate (coarse granules) | 1250 | 1500 | 750 | 350 |
| Sodium carbonate (anhydrous) | 158 | — | 158 | 158 |
| Citric acid (anhydrous) | 923 | — | — | — |
| Adipic acid | — | 1050 | — | — |
| Sodium dihydrogen citrate | — | — | 1050 | — |
| Disodium hydrogen citrate | — | — | — | 1250 |
| Sweetner | 10 | 10 | 10 | 10 |
| Flavouring | 20 | 20 | 20 | 20 |

EXAMPLE 1

A powder of Formulation A was prepared in conditions of less than 40% relative humidity as follows:

The metoclopramide salt (60 mesh), the sweetener and flavouring (30 mesh), the sodium carbonate (50 mesh) and an equal volume of the paracetamol D.C. (30 mesh) were mixed for 5 minutes in a planetary mixer. The remainder of the paracetamol was added to the mixture, and mixing was continued for a further 5 minutes, followed by addition of the citric acid (30 mesh) and 5 minutes' mixing, and addition of the sodium bicarbonate (30 mesh) and 30 minutes' mixing.

The mixture was filled into a sachet.

The sachet contents were then dissolved in 50 ml of water.

EXAMPLE 2

A powder of Formulation B was prepared by the method of Example 1, substituting adipic acid for citric acid; and filled into a sachet.

The sachet contents were then dissolved in 50 ml of water.

EXAMPLE 3

A powder of Formulation A was prepared as follows:

The sweetener (30 mesh) and citric acid (30 mesh) were mixed in a planetary mixer for 5 minutes. The metoclopramide salt was dissolved in water and the mixture and the solution were wet granulated through a 10 mesh sieve, and the granulate was dried for 16 hr in a 50° C. oven.

Subsequent operations were carried out in conditions of less then 40% relative humidity.

The granulate, sodium carbonate and flavouring were mixed in a planetary mixer for 5 minutes. The paracetamol D.C. was added and mixing carried out for a further 5 minutes, followed by addition of the bicarbonate followed by 30 minutes' mixing.

The mixture was filled into a sachet.

The sachet contents were then dissolved in 50 ml of water.

EXAMPLE 4

A powder of Formulation B was prepared by the method of Example 3, substituting adipic acid for citric acid, and filled into a sachet.

EXAMPLE 5

A powder of Formulation C was prepared by the method of Example 1, substituting sodium dihydrogen citrate for citric acid, and filled into a sachet.

The sachet contents were then dissolved in 50 ml water.

EXAMPLE 6

A powder of Formulation D was prepared by the method of Example 1, substituting disodium hydrogen citrate for citric acid and filled into a sachet.

The sachet contents were then dissolved in 50 ml water.

What we claim is:

1. An analgesic effervescent powder comprising paracetamol D.C. and metoclopramide or an acid addition salt thereof in a weight ratio of from 80:1 to 120:1 respectively.

2. A powder according to claim 1 wherein the metoclopramide or its acid addition salt is present at 0.05 to 0.4 percent by weight.

3. A powder according to claim 1 containing (a) sodium bicarbonate and (b) sodium dihydrogen citrate or disodium hydrogen citrate.

4. A unit of the powder according to claim 1 containing from 0.4 to 0.6 g of paracetamol D.C. and 4 to 6 mg of metoclopramide or an acid addition salt thereof.

5. A method of treating migraine headache, which method comprises administering to the sufferer a therapeutically effective amount of paracetamol D.C. and metoclopramide or an acid addition salt thereof in the aqueous solution derived from the reaction of a powder according to claim 1 and water.

* * * * *